United States Patent
Nirkhe

(10) Patent No.: US 11,754,196 B2
(45) Date of Patent: Sep. 12, 2023

(54) ELECTROMAGNETIC ACTUATION OF ELASTOMERIC VALVE FOR FLUID FLOW CONTROL

(71) Applicant: Johnson & Johnson Surgical Vision, Inc., Irvine, CA (US)

(72) Inventor: Chetan P. Nirkhe, Aliso Viejo, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 57 days.

(21) Appl. No.: 16/167,421

(22) Filed: Oct. 22, 2018

(65) Prior Publication Data

US 2020/0124199 A1    Apr. 23, 2020

(51) Int. Cl.
*F16K 31/06* (2006.01)

(52) U.S. Cl.
CPC .................................. *F16K 31/06* (2013.01)

(58) Field of Classification Search
CPC .. F16K 7/12–14; F16K 31/06; F16K 31/0672; F16K 7/045; H01F 7/086
USPC ................... 251/129.16, 7, 129.17
See application file for complete search history.

(56) References Cited

U.S. PATENT DOCUMENTS

| | | | |
|---|---|---|---|
| 2,550,297 A * | 4/1951 | Ray | F16K 31/0679 361/161 |
| 2,911,183 A | 11/1959 | Matthews et al. | |
| 3,645,293 A * | 2/1972 | Pedersen | F15B 5/003 137/861 |
| 3,740,019 A | 6/1973 | Kessell et al. | |
| 3,809,123 A * | 5/1974 | Heimann | F16K 31/082 137/625.5 |
| 3,817,488 A * | 6/1974 | Mack | F16K 31/06 251/30.03 |
| 3,942,759 A * | 3/1976 | Passera | F16K 31/06 251/129.08 |
| 4,196,751 A * | 4/1980 | Fischer | F16K 31/0627 137/625.65 |
| 4,579,137 A * | 4/1986 | Brandt, Jr. | F15B 5/003 137/82 |
| 4,706,687 A | 11/1987 | Rogers et al. | |
| 4,848,727 A * | 7/1989 | Nanbu | F16K 31/0658 251/129.16 |
| 5,188,334 A * | 2/1993 | Yoshii | F16K 7/045 251/7 |
| 5,424,704 A * | 6/1995 | Dolle | F02M 51/0639 251/129.18 |

(Continued)

FOREIGN PATENT DOCUMENTS

| | | |
|---|---|---|
| CN | 204805613 U | 11/2015 |
| DE | 3024435 A1 | 1/1982 |

(Continued)

*Primary Examiner* — Matthew W Jellett
(74) *Attorney, Agent, or Firm* — Johnson & Johnson Surgical Vision, Inc.

(57) ABSTRACT

Actuation of an elastomeric valve with an electromagnet is disclosed wherein an elastomeric valve material may comprise a steel disc embedded in its wall to control the flow of fluid. In response to an electric current being applied to an electromagnet, a magnetic field attracts a disc embedded in the elastomeric valve material. The elastomeric valve would then move towards the electromagnet to create a seal, thereby blocking the flow of fluid.

9 Claims, 4 Drawing Sheets

(56) References Cited

U.S. PATENT DOCUMENTS

| | | | | |
|---|---|---|---|---|
| 5,474,100 A * | 12/1995 | Nishijima | ........... | G05D 16/2013 |
| | | | | 137/544 |
| 5,628,491 A * | 5/1997 | Krone | ........................ | A01J 5/14 |
| | | | | 251/129.21 |
| 5,645,264 A * | 7/1997 | Kah, Jr. | ................... | F16K 7/126 |
| | | | | 251/126 |
| 6,068,010 A * | 5/2000 | Reinicke | ................... | B64G 1/26 |
| | | | | 137/1 |
| 6,116,576 A * | 9/2000 | Hoglund | ................. | F16K 31/06 |
| | | | | 251/129.17 |
| 6,339,366 B1 * | 1/2002 | Meisiek | .............. | F16K 31/0655 |
| | | | | 335/282 |
| 6,592,583 B2 | 7/2003 | Hirano et al. | | |
| 6,786,468 B2 * | 9/2004 | Schroeder | ........... | F16K 31/0658 |
| | | | | 251/129.17 |
| 6,910,674 B2 * | 6/2005 | Niemela | ................ | A61M 16/20 |
| | | | | 251/129.17 |
| 7,267,113 B2 | 9/2007 | Tsuge et al. | | |
| 9,561,321 B2 * | 2/2017 | Sorensen | ............ | A61M 3/0279 |
| 2006/0207663 A1 | 9/2006 | Tsuge et al. | | |
| 2008/0077077 A1 | 3/2008 | Williams | | |
| 2011/0042597 A1 | 2/2011 | Huculak et al. | | |
| 2013/0150782 A1 | 6/2013 | Sorensen et al. | | |
| 2016/0228889 A1 * | 8/2016 | Maruyama | ............ | F16K 31/128 |
| 2020/0148524 A1 * | 5/2020 | Ohrem | ...................... | B67C 3/26 |

FOREIGN PATENT DOCUMENTS

| | | |
|---|---|---|
| DE | 19851143 A1 | 5/2000 |
| DE | 202017100507 U1 | 5/2018 |
| EP | 2376035 A2 | 10/2011 |
| RU | 140248 U1 | 5/2014 |
| WO | 2015200878 A1 | 12/2015 |

* cited by examiner

ELECTROMAGNETIC ACTUATION OF ELASTOMERIC VALVE FOR FLUID FLOW CONTROL

FIELD OF THE INVENTION

The present invention relates to phacoemulsification fluidics system control, and, more particularly, an elastomeric valve for fluid flow control.

BACKGROUND

Cataracts affect more than 22 million Americans age 40 and older. And as the U.S. population ages, more than 30 million Americans are expected to have cataracts by the year 2020. Cataract surgery entails the removal of a lens of an eye that has developed clouding of the eye's natural lens, or opacification. As a result of opacification, light is unable to travel to the retina, thereby causing vision loss. Once vision becomes impaired, cataract surgery is a viable option with a high level of success. During cataract surgery, a surgeon replaces the clouded lens with an intraocular lens (IOL).

Certain surgical procedures, such as phacoemulsification surgery, have been successfully employed in the treatment of certain ocular problems, such as cataracts. Phacoemulsification surgery utilizes a small corneal incision to insert the tip of at least one phacoemulsification handheld surgical implement, or handpiece, through the corneal incision. The handpiece includes a needle which is ultrasonically driven once placed within the incision to emulsify the eye lens, or to break the cataract into small pieces. The broken cataract pieces or emulsified eye lens may subsequently be removed using the same handpiece, or another handpiece, in a controlled manner. The surgeon may then insert a lens implant into the eye through the incision. The incision is allowed to heal, and the result for the patient is typically significantly improved eyesight.

During the phacoemulsification process for cataract removal, a disposable plastic cassette is generally used to collect effluent material. The disposable plastic cassette may consist of a tubing cassette which has flow paths for fluid and one or more valves to stop fluid flow or adjust fluid flow. In the prior art, the valve actuation utilized for commercial phacoemulsification cassette packs is performed by means of a plunger attached to a solenoid which moves forward to push an elastomeric material such as silicone that would obstruct the flow of fluid. The problem with solenoid actuation is that the force exerted by the solenoid drops with time as the solenoid is actuated and hence is inconsistent. Additionally, the force from solenoid changes with stroke length.

One approach taught by U.S. Pat. No. 9,561,321 B2 utilizes rotary moveable cartridge valves which are injection molded and engage in a complementary socket that when actuated reduces the orifice size and obstructs the flow of fluid for ophthalmic cassette application.

BRIEF SUMMARY OF THE INVENTION

The disclosed invention is directed towards the actuation of an elastomeric valve with an electromagnet. In a preferred embodiment, the elastomeric valve material may comprise a flexible rubber-like material with a steel disc embedded in its wall. Other material other than a steel disc may be used in alternative embodiments, as long as the material attracts an electromagnet. In response to an electric current being applied to an electromagnet, a magnetic field attracts, in accordance with the preferred embodiment, the steel disc embedded in the elastomeric valve material. The elastomeric valve would then move towards the electromagnet. In the preferred embodiment, the electromagnet would be placed opposite the elastomeric valve that attracts the disc and closes the pathway of fluid flowing in the channel across.

The disclosed invention may provide an elastomeric actuator valve, comprising a housing, an electromagnet contained by the housing, an elastomeric valve opposite the housing, one or more magnetic materials contained by the elastomeric valve, and a fluid pathway between the housing and the elastomeric valve. The elastomeric valve may be attracted to the housing in response to activation of the electromagnet thereby closing the fluid pathway and causing a seal between the housing and the elastomeric valve. The elastomeric valve may be repelled from the housing in response to deactivation of the electromagnet thereby opening the fluid pathway. The elastomeric valve may also comprise one or more magnetic materials such as a steel disc.

BRIEF DESCRIPTION OF THE DRAWINGS

This disclosure is illustrated by way of example and not by way of limitation in the accompanying figure(s). The figure(s) may, alone or in combination, illustrate one or more embodiments of the disclosure. Elements illustrated in the figure(s) are not necessarily drawn to scale. Reference labels may be repeated among the figures to indicate corresponding or analogous elements.

The detailed description makes reference to the accompanying figures in which.

DETAILED DESCRIPTION

The figures and descriptions provided herein may have been simplified to illustrate aspects that are relevant for a clear understanding of the herein described apparatuses, systems, and methods, while eliminating, for the purpose of clarity, other aspects that may be found in typical similar devices, systems, and methods. Those of ordinary skill may thus recognize that other elements and/or operations may be desirable and/or necessary to implement the devices, systems, and methods described herein. But because such elements and operations are known in the art, and because they do not facilitate a better understanding of the present disclosure, for the sake of brevity a discussion of such elements and operations may not be provided herein. However, the present disclosure is deemed to nevertheless include all such elements, variations, and modifications to the described aspects that would be known to those of ordinary skill in the art.

Embodiments are provided throughout so that this disclosure is sufficiently thorough and fully conveys the scope of the disclosed embodiments to those who are skilled in the art. Numerous specific details are set forth, such as examples of specific components, devices, and methods, to provide a thorough understanding of embodiments of the present disclosure. Nevertheless, it will be apparent to those skilled in the art that certain specific disclosed details need not be employed, and that exemplary embodiments may be embodied in different forms. As such, the exemplary embodiments should not be construed to limit the scope of the disclosure. As referenced above, in some exemplary embodiments, well-known processes, well-known device structures, and well-known technologies may not be described in detail.

Figure 1A:
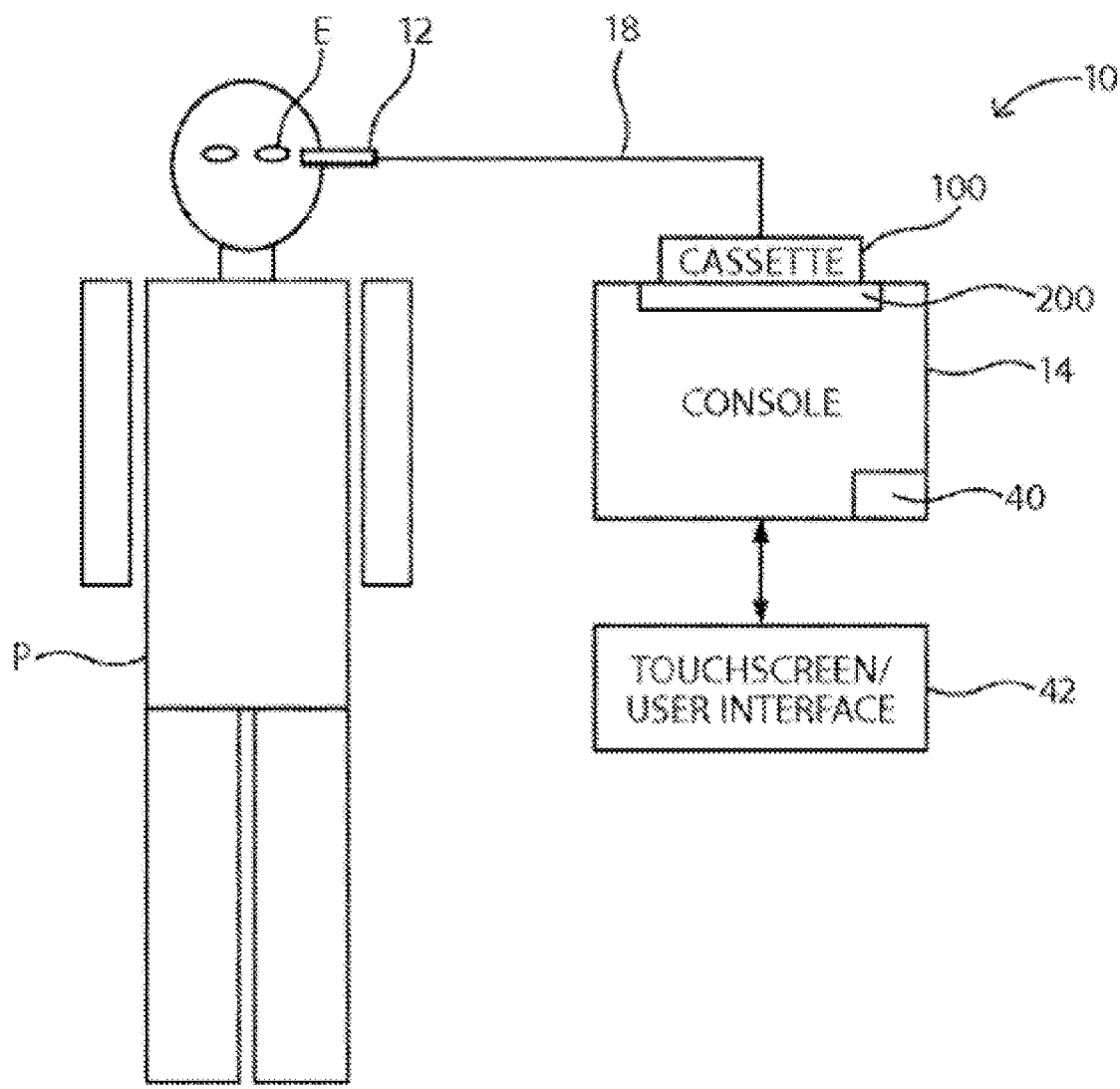
FIG. 1A schematically illustrates an eye treatment system in which a cassette couples an eye treatment probe with an eye treatment console.

Referring to FIG. 1A, a system 10 for treating an eye E of a patient P generally includes an eye treatment probe handpiece 12 coupled to a console 14 by a cassette 100 mounted on the console. Handpiece 12 may include a handle for manually manipulating and supporting an insertable probe tip. The probe tip has a distal end which is insertable into the eye, with one or more lumens in the probe tip allowing irrigation fluid to flow from the console 14 and/or cassette 100 into the eye. Aspiration fluid may also be withdrawn through a lumen of the probe tip, with the console 14 and cassette 100 generally including a vacuum aspiration source, a positive displacement aspiration pump, or both to help withdraw and control a flow of surgical fluids into and out of eye E. As the surgical fluids may include biological materials that should not be transferred between patients, cassette 100 will often be disposable or comprise a disposable (or alternatively, re-sterilizable) structure, with the surgical fluids being transmitted through conduits of the cassette that avoid direct contact in between those fluids and the components of console 14.

When a distal end of the probe tip of handpiece 12 is inserted into an eye E, for example, for removal of a lens of a patient with cataracts, an electrical conductor and/or pneumatic line (not shown) may supply energy from console 14 to an ultrasound transmitter of the handpiece, a cutter mechanism, or the like. Alternatively, the handpiece 12 may be configured as an irrigation/aspiration (I/A) or vitrectomy handpiece. Also, the ultrasonic transmitter may be replaced by other means for emulsifying a lens, such as a high energy laser beam. The ultrasound energy from handpiece 12 helps to fragment the tissue of the lens, which can then be drawn into a port of the tip by aspiration flow. So as to balance the volume of material removed by the aspiration flow, an irrigation flow through handpiece 12 (or a separate probe structure) may also be provided, with both the aspiration and irrigations flows being controlled by console 14.

So as to avoid cross-contamination between patients and/or to avoid incurring excessive expenditures for each procedure, cassette 100 and its conduit 18 may be disposable. Alternatively, the conduit or tubing may be disposable, with the cassette body and/or other structures of the cassette being sterilizable. Regardless, the disposable components of the cassette are typically configured for use with a single patient and may not be suitable for sterilization. The cassette will interface with reusable (and often quite expensive) components of console 14, which may include one or more peristaltic pump rollers, a Venturi or other vacuum source, a controller 40, and the like.

Controller 40 may include an embedded microcontroller and/or many of the components common to a personal computer, such as a processor, data bus, a memory, input and/or output devices (including a touch screen user interface 42), and the like. Controller 40 will often include both hardware and software, with the software typically comprising machine readable code or programming instructions for implementing one, some, or all of the methods described herein. The code may be embodied by a tangible media such as a memory, a magnetic recording media, an optical recording media, or the like. Controller 40 may have (or be coupled to) a recording media reader, or the code may be transmitted to controller 40 by a network connection such as an internet, an intranet, an Ethernet, a wireless network, or the like. Along with programming code, controller 40 may include stored data for implementing the methods described herein, and may generate and/or store data that records parameters corresponding to the treatment of one or more patients. Many components of console 14 may be found in or modified from known commercial phacoemulsification.

Figure 1B:
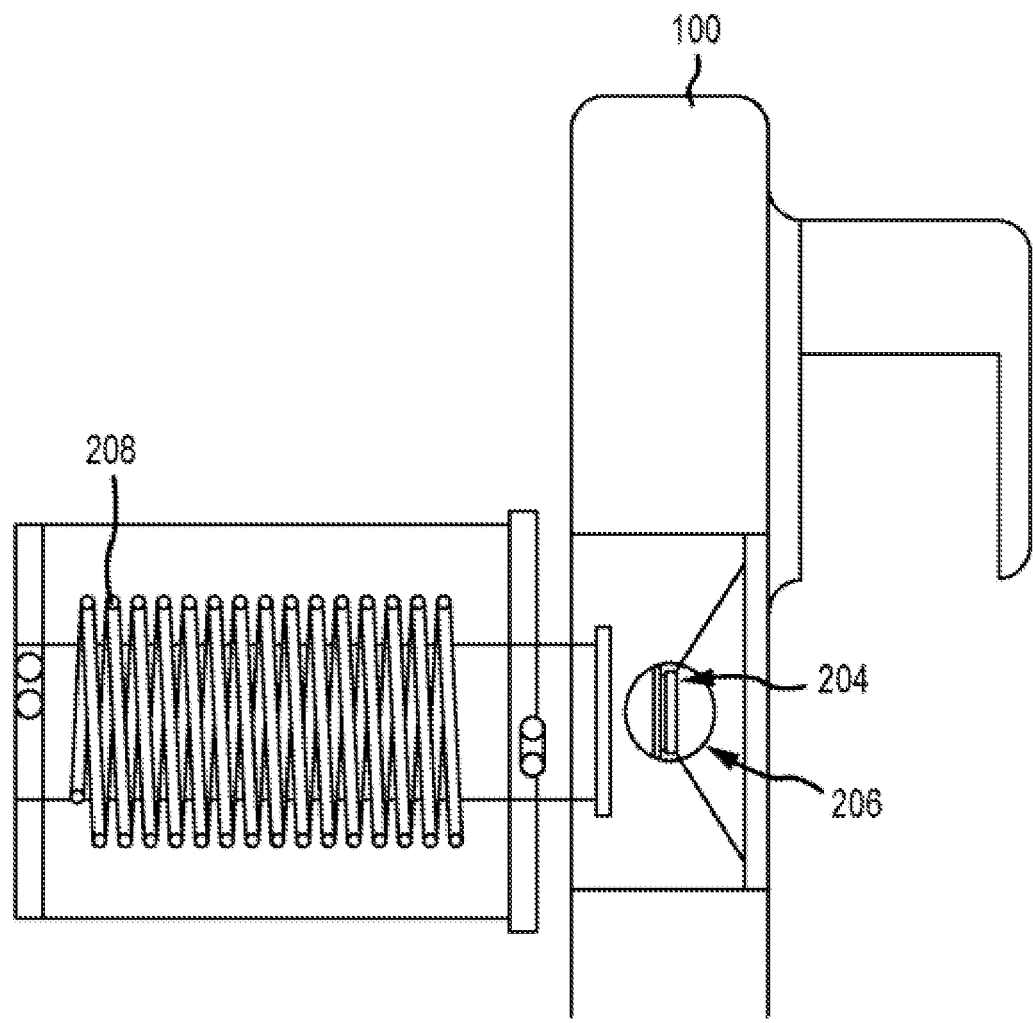
FIGS. 1B and 1C illustrate a cassette used with an eye treatment console having an electromagnet in accordance with the disclosed invention.
Figure 1C:
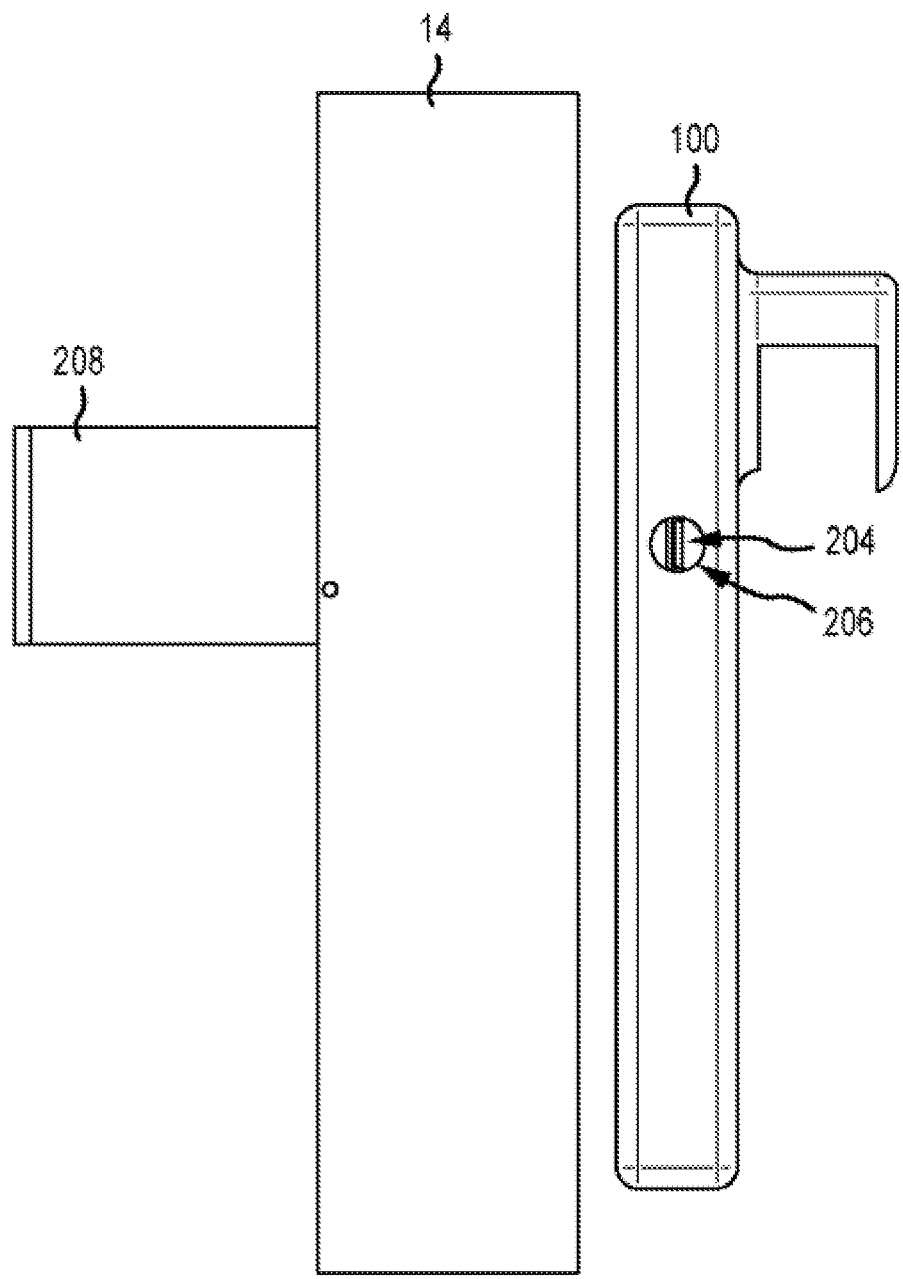

In illustrative embodiments, a surgical cassette 100, such as the one illustrated in FIGS. 1B and 1C, may be configured to be coupled and removed from the console 14 after use during a surgical procedure and may include at least one valve 204. In conjunction with electromagnet 208, fluid flow may be controlled through flow path 206 by the at least one valve 204, as described below.

Figure 2A:
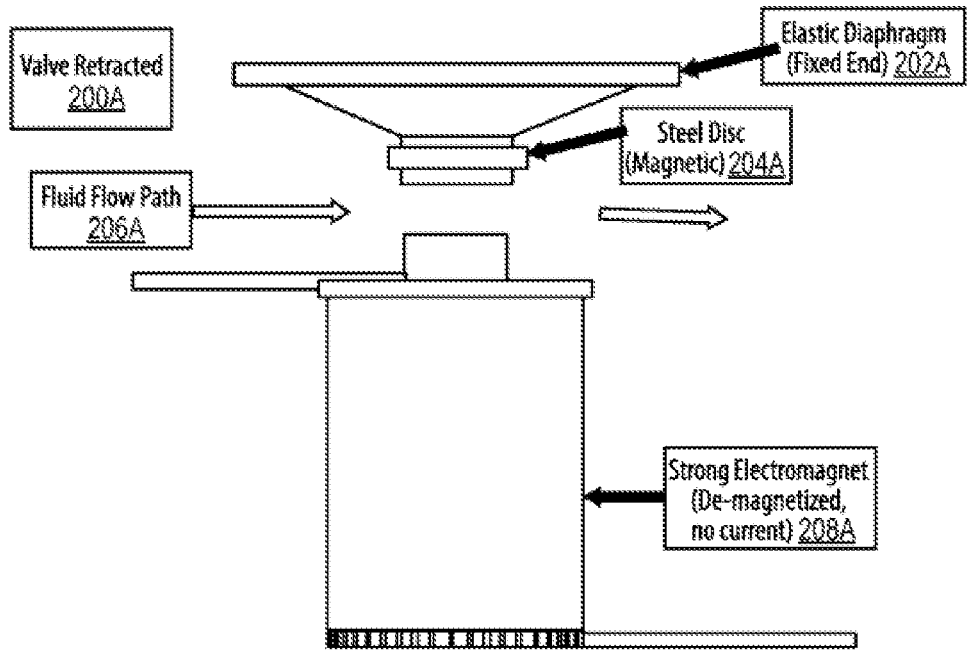
FIGS. 2A and 2B illustrate an elastomeric valve for fluid flow control in accordance with the disclosed invention.
Figure 2B:
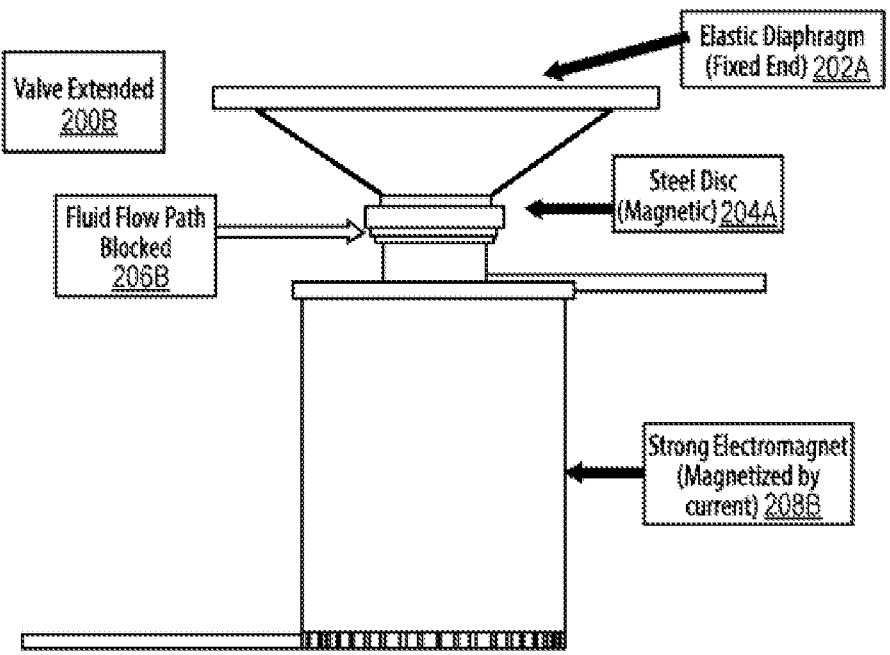

FIGS. 2A and 2B illustrate embodiments of a valve which may, for example, be used in a surgical cassette of the present invention. The valve may be electromagnetic and may, for example, be controllable through a surgical console. The use of an electromagnetic valve over a traditional valve, such as one associated with a solenoid, allows for a smaller valve size as a solenoid may be bulky in construction. Further, an electromagnetic valve has no need for the use of an additional plunger attachment to interface with the valve, therefore reducing the number of components for assembly. Additionally, an electromagnetic valve does not experience any variation in force due to stroke length setting such as when assembling a plunger onto a solenoid.

FIG. 2A illustrates an embodiment of an electromagnetic valve 200A in a retracted state. The valve may include, on a fixed end, an elastomeric diaphragm 202A connected to a steel disc 204A. The steel disc 204A may have magnetic properties. The use of a steel disc is merely meant to be exemplary. It is understood that other magnetic materials may be utilized, such as iron, nickel, cobalt or other rare earth materials that exhibit magnetic behavior. Disc 204A may also take on different geometrical shapes. As shown, the disc 204A in its simplest form may take on a circular shape. However, it is understood that the circular shape is not meant to be limiting. For example, the disc may take on an oval or ellipsoid shape, among others. In yet another embodiment, the disc 204A may take on a custom shape formation to match the fluid flow path 206 and a mating surface. FIG. 2A shows the magnetic material embedded in the wall to form a disc being in a relaxed state. In an alternative embodiment, the magnetic material, such as the disc, may be affixed to the inside of the elastomeric diaphragm 202A, such as with glue or any other type of adhesive substance. In another exemplary embodiment, the magnetic material may be fully or partially encased within the elastomeric diaphragm. If partially encased, portions of the magnetic material may be exposed.

For example, the valve is open and allows the flow along fluid flow path 206A. The valve may include a strong electromagnet 208A that, when demagnetized (e.g., no current), enables disc 204A to be in a relaxed, or retracted, state. In yet another embodiment, fluid flow rate may be controlled by a combination of magnetization and demagnetization resulting in a narrowing of the pathway 206A.

FIG. 2B illustrates an embodiment of an electromagnetic valve 200B in an extended state. The valve may include, on a fixed end, an Elastomeric Diaphragm 202A connected to a steel disc 204A. In this example, elastomeric diaphragm 202A may be attached to the cassette body and retract from the electromagnet 208A. The steel disc 204A may have magnetic properties as described above with respect to FIG. 2A. FIG. 2B shows the magnetic material embedded in the wall to form a disc being in a relaxed state. For example, the valve is closed and blocks the flow of fluid along Fluid Flow Path 206B. Fluid flow path 206B may be a rigid molded channel in a shape that is complementary to the disc shape, for example. The valve may include a strong electromagnet 208B that, when magnetized (e.g., magnetized by current), enables and causes disc 204A to be in an extended state.

In an alternative embodiment, the diaphragm 202A and disc 204A may use magnetic materials embedded in an elastomeric matrix and may use electromagnet 208A to repel the valve to an open state. In this embodiment, when the electromagnet 208A is demagnetized, or a non-magnetized state, the elastomeric matrix magnet will not be attracted to the electromagnet due to the presence of magnetic materials, such as an iron core, for example.

In yet another alternative embodiment of the disclosed invention, the diaphragm 202A and disc 204A may be comprised of elastomeric rubber valve materials coated with a thin layer of magnetic material (for e.g. a layer of nickel particles/fibers), such as magnetic fibers, which may attract electromagnet 208A. The thin layer of magnetic fiber coating may be utilized in place of an embedded magnetic/steel disc.

Elastomeric elements of the valve may help create a seal and completely occlude fluid flow by compressing the elastomer when the disc is attracted. When the electromagnet current stops flowing through a coil of the electromagnet, the elastomeric valve is no longer attracted towards the electromagnet and thus retracts back to open the flow path.

In an embodiment of the present invention, the electromagnetic valve may be controlled by aspects of controller 40 which may be operatively connected to the electromagnetic coil(s). The controller 40 may calculate an opening/closing timing for the valve based on various data, such as, real time operating parameters, user defined parameters, and/or a combination of both. The CPU may alternatively energize the electromagnetic coil(s) at the opening/closing timing, thus opening or closing the valve. Similarly, the valve may be controlled such that a partial flow may occur by only partially actuating the valve. For example, the controller may only activate a portion of the electromagnet which may only draw a portion of the valve into a substantially closed position allowing for more control over the flow of fluid.

Those of skill in the art will appreciate that the herein described apparatuses, engines, devices, systems and methods are susceptible to various modifications and alternative constructions. There is no intention to limit the scope of the invention to the specific constructions described herein. Rather, the herein described systems and methods are intended to cover all modifications, alternative constructions, and equivalents falling within the scope and spirit of the disclosure, any appended claims and any equivalents thereto.

In the foregoing detailed description, it may be that various features are grouped together in individual embodiments for the purpose of brevity in the disclosure. This method of disclosure is not to be interpreted as reflecting an intention that any subsequently claimed embodiments require more features than are expressly recited.

Further, the descriptions of the disclosure are provided to enable any person skilled in the art to make or use the disclosed embodiments. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but rather is to be accorded the widest scope consistent with the principles and novel features disclosed herein.

The invention claimed is:

1. An elastomeric actuator valve comprising:
   a housing,
   wherein at least a portion of one of the housing or the elastomeric actuator valve is housed in a surgical cassette;
   an electromagnet contained by the housing and configured to activate and deactivate;
   a diaphragm comprising elastomeric rubber valve materials;
   a disc arranged on the diaphragm, the disc comprising a layer of a single magnetic material or a magnetic alloy coating the diaphragm and being configured to interact with the electromagnet, the disc comprising a custom shape formation to match a pathway and a mating surface, and the disc being affixed to an inside of the diaphragm via an adhesive substance; and
   wherein the pathway is between the housing and a combination of the diaphragm and the disc, and the pathway comprising a rigid molded channel in a shape that is complementary to the custom shape formation of the disc,
   wherein activation and deactivation of the electromagnet causes the layer to be attracted and repelled thereby respectively narrowing and widening the pathway and adjusting fluid flow along the pathway,
   wherein, in accordance with the activation and the deactivation of the electromagnet, the layer of the single magnetic material or the magnetic alloy:
      is repelled from the housing in response to the deactivation of the electromagnet to cause the diaphragm to retract across and open the pathway, and
      is attracted to the housing in response to the activation of the electromagnet to cause the combination to cross, seal, and occlude the fluid flow through the pathway,
   wherein the interaction between the layer of the single magnetic material or the magnetic alloy and the electromagnet provides a force across a stroke length of the elastomeric actuator valve and
   wherein the diaphragm and the disc comprise a movement that is perpendicular to the fluid flow of the pathway.

2. The elastomeric actuator valve of claim 1, wherein the pathway is an air pathway.

3. A method for actuating an elastomeric portion of a valve with respect to an electromagnet and a pathway, the elastomeric portion comprising a diaphragm comprising elastomeric rubber valve materials, a disc arranged on the diaphragm, the disc comprising a layer of a single magnetic material or a magnetic alloy coating the diaphragm, and the layer of the single magnetic material or the magnetic alloy being configured to interact with the electromagnet, the method comprising:
   attracting the layer of the single magnetic material or the magnetic alloy to the electromagnet to cause a combination of the diaphragm and the disc to cross, seal, and occlude fluid flow through the pathway in response to activation of the electromagnet, the disc comprising a custom shape formation to match a pathway and a mating surface, and the disc being affixed to an inside of the diaphragm via an adhesive substance; and; and
   repelling the layer of the single magnetic material or the magnetic alloy from the electromagnet to cause the diaphragm to retract across and open a fluid pathway in response to deactivation of the electromagnet;

wherein movement of the combination is at least partially indicative of at least one parameter controlled by a surgical console, wherein the interaction between the layer of the single magnetic material or the magnetic alloy and the electromagnet provides a force across a stroke length of the combination, wherein activation and deactivation of the electromagnet causes the layer to be attracted and repelled thereby respectively narrowing and widening the fluid pathway and adjusting the fluid flow along the fluid pathway, wherein the diaphragm and the disc comprise a movement that is perpendicular to the fluid flow of the pathway, and wherein the pathway comprises a rigid molded channel in a shape that is complementary to the custom shape formation of the disc.

4. The method of claim 3, wherein the pathway is an air pathway.

5. The method of claim 3, wherein attracting and repelling respectively causes narrowing and widening of the pathway to adjust fluid flow.

6. An actuator valve system comprising:
a surgical cassette comprising a fluid channel;
a diaphragm comprising elastomeric rubber valve materials;
a disc arranged on the diaphragm, the disc comprising a layer of a single magnetic material or a magnetic alloy coating the diaphragm and being configured to interact with an electromagnet, the disc comprising a custom shape formation to match a pathway and a mating surface, and the disc being affixed to an inside of the diaphragm via an adhesive substance; and; and
the electromagnet configured to activate and deactivate, wherein the layer of the single magnetic material or the magnetic alloy:

is repelled from the electromagnet in response to the deactivation of the electromagnet to cause the diaphragm to retract across and open the fluid channel, and is attracted to the electromagnet in response to the activation of the electromagnet to cause a combination of the diaphragm and the disc to cross, seal, and occlude fluid flow through the fluid channel, wherein the interaction between the layer of the single magnetic material or the magnetic alloy and the electromagnet provides a force across a stroke length of the actuator valve system, wherein activation and deactivation of the electromagnet causes the layer to be attracted and repelled thereby respectively narrowing and widening the fluid channel and adjusting the fluid flow along the fluid channel, wherein the diaphragm and the disc comprise a movement that is perpendicular to the fluid flow of the pathway, and wherein the pathway comprises a rigid molded channel in a shape that is complementary to the custom shape formation of the disc.

7. The actuator valve system of claim 6, further comprising:
a console communicatively coupled to the electromagnet and configured to activate and deactivate the electromagnet.

8. The elastomeric actuator valve of claim 1, wherein the single magnetic material or the magnetic alloy comprises magnetic fibers.

9. The elastomeric actuator valve of claim 1, wherein elastomeric rubber valve materials of the elastomeric actuator valve compress to create the seal and occlude the fluid flow through the pathway when the layer of the single magnetic material or the magnetic alloy is attracted.

* * * * *